US008884036B2

(12) United States Patent
De Silva et al.

(10) Patent No.: US 8,884,036 B2
(45) Date of Patent: Nov. 11, 2014

(54) PRODUCTION OF HYDROXYMETHYLFURFURAL FROM LEVOGLUCOSENONE

(71) Applicant: E I Du Pont De Nemours and Company, Wilmington, DE (US)

(72) Inventors: Wathudura Indika Namal De Silva, Rahway, NJ (US); Joachim C Ritter, Wilmington, DE (US); Christina S Stauffer, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/729,507

(22) Filed: Dec. 28, 2012

(65) Prior Publication Data

US 2013/0172580 A1 Jul. 4, 2013

Related U.S. Application Data

(60) Provisional application No. 61/582,067, filed on Dec. 30, 2011.

(51) Int. Cl.
| | | |
|---|---|---|
| C07D 307/40 | (2006.01) | |
| C07D 307/38 | (2006.01) | |
| C07D 307/36 | (2006.01) | |
| C07D 307/46 | (2006.01) | |
| C07C 29/141 | (2006.01) | |
| C07D 309/06 | (2006.01) | |
| C07C 29/132 | (2006.01) | |

(52) U.S. Cl.
CPC ............ *C07D 307/46* (2013.01); *C07C 29/141* (2013.01); *C07D 309/06* (2013.01); *C07C 29/132* (2013.01)
USPC ............................ 549/502; 594/502; 568/865

(58) Field of Classification Search
USPC .......................................... 568/865; 549/502
See application file for complete search history.

(56) References Cited

U.S. PATENT DOCUMENTS

| | | | |
|---|---|---|---|
| 2,082,025 A | 6/1937 | Peters | |
| 2,201,347 A | 5/1940 | Rittmeister | |
| 2,440,929 A | 5/1948 | Frederick | |
| 2,768,213 A | 10/1956 | Whetstone et al. | |
| 3,070,633 A | 12/1962 | Utne et al. | |
| 3,083,236 A | 3/1963 | Utne et al. | |
| 3,189,651 A | 6/1965 | Ellery et al. | |
| 3,215,742 A | 11/1965 | Horlenko et al. | |
| 3,223,714 A | 12/1965 | Manly et al. | |
| 3,268,588 A | 8/1966 | Horlenko et al. | |
| 3,270,059 A | 8/1966 | Winderl et al. | |
| 3,917,707 A | 11/1975 | Williams et al. | |
| 3,933,930 A | 1/1976 | Dougherty et al. | |
| 4,254,059 A | 3/1981 | Grey | |
| 4,400,468 A | 8/1983 | Faber | |
| 4,401,823 A | 8/1983 | Arena | |
| 4,780,552 A | 10/1988 | Wambach et al. | |
| 5,112,994 A | 5/1992 | Koseki et al. | |
| 5,210,335 A | 5/1993 | Schuster et al. | |
| 5,412,111 A | 5/1995 | Matsumoto et al. | |
| 5,538,891 A | 7/1996 | Schneider et al. | |
| 5,696,303 A | 12/1997 | Darsow et al. | |
| 5,981,769 A | 11/1999 | Baur et al. | |
| 6,008,418 A | 12/1999 | Baur et al. | |
| 6,087,296 A | 7/2000 | Harper et al. | |
| 6,147,208 A | 11/2000 | Achhammer et al. | |
| 6,265,602 B1 | 7/2001 | Voit et al. | |
| 6,403,845 B1 | 6/2002 | Pfeffinger et al. | |
| 6,407,294 B1 | 6/2002 | Breitscheidel et al. | |
| 6,433,192 B1 | 8/2002 | Fischer et al. | |
| 6,462,220 B1 | 10/2002 | Luyken et al. | |
| 6,593,481 B1 | 7/2003 | Manzer | |
| 6,818,781 B2 | 11/2004 | Bhatia | |
| 7,019,155 B2 | 3/2006 | Manzer | |
| 7,230,145 B2 | 6/2007 | Kadowaki et al. | |
| 8,053,608 B2 | 11/2011 | Kouno et al. | |
| 8,053,615 B2 | 11/2011 | Cortright et al. | |
| 8,501,989 B2 | 8/2013 | Boussie et al. | |
| 8,524,925 B2 | 9/2013 | Sabesan et al. | |
| 8,669,393 B2 | 3/2014 | Boussie et al. | |
| 2003/0212298 A1 | 11/2003 | Brasse et al. | |
| 2006/0014988 A1 | 1/2006 | Fischer et al. | |
| 2007/0287845 A1 | 12/2007 | Lilga et al. | |
| 2008/0200698 A1 | 8/2008 | Reichert et al. | |
| 2009/0156841 A1 | 6/2009 | Sanborn et al. | |

(Continued)

FOREIGN PATENT DOCUMENTS

| | | |
|---|---|---|
| CA | 2800797 A1 | 12/2011 |
| CN | 101628875 A | 1/2010 |

(Continued)

OTHER PUBLICATIONS

Buntara, Teddy et al., Caprolactam from Renewable Resources: Catalytic Conversion of 5-Hydroxymethylfurfural into Caprolactone, Angewandte Chemie International Edition, 2011, pp. 1-6, vol. 50.

(Continued)

*Primary Examiner* — Elvis O Price

(57) ABSTRACT

Disclosed are processes comprising contacting an aqueous reaction mixture having an initial pH between about 3 and about 6 and comprising levoglucosenone with a catalyst, and heating the reaction mixture to form a product mixture comprising 5-hydroxymethyl-2-furfural. The processes may further comprise heating the product mixture comprising 5-hydroxymethyl-2-furfural in the presence of hydrogen and a hydrogenation catalyst to form a second product mixture comprising one or more of 2,5-furandimethanol, tetrahydrofuran 2,5-dimethanol, 1,2,6-hexanetriol, 2-hydroxymethyltetrahydropyran, and 1,6-hexanediol.

13 Claims, No Drawings

(56) References Cited

U.S. PATENT DOCUMENTS

| | | |
|---|---|---|
| 2009/0314992 A1 | 12/2009 | Pinkos et al. |
| 2010/0113841 A1 | 5/2010 | Suzuki et al. |
| 2010/0216958 A1 | 8/2010 | Peters et al. |
| 2010/0274030 A1 | 10/2010 | Bevinakatti et al. |
| 2010/0317822 A1 | 12/2010 | Boussie et al. |
| 2011/0040131 A1 | 2/2011 | Kouno et al. |
| 2011/0071306 A1 | 3/2011 | Robinson |
| 2011/0218318 A1 | 9/2011 | Boussie et al. |
| 2011/0263916 A1 | 10/2011 | Bao et al. |
| 2011/0312051 A1 | 12/2011 | Kalnes et al. |
| 2012/0010419 A1 | 1/2012 | Pinkos et al. |
| 2012/0022298 A1 | 1/2012 | Pinkos et al. |
| 2012/0035399 A1 | 2/2012 | Abillard et al. |
| 2012/0059174 A1 | 3/2012 | Abillard et al. |
| 2012/0116122 A1 | 5/2012 | Feist et al. |
| 2012/0172579 A1 | 7/2012 | Qiao et al. |
| 2013/0172578 A1 | 7/2013 | Allgeier et al. |
| 2013/0172579 A1 | 7/2013 | Desilva et al. |
| 2013/0172586 A1 | 7/2013 | Desilva et al. |
| 2013/0172629 A1 | 7/2013 | Allgeier et al. |
| 2013/0184495 A1 | 7/2013 | Dias et al. |
| 2013/0231505 A1 | 9/2013 | Allgeier et al. |
| 2013/0289311 A1 | 10/2013 | Allgeier et al. |
| 2013/0289312 A1 | 10/2013 | Allgeier et al. |
| 2013/0289318 A1 | 10/2013 | Allgeier et al. |
| 2013/0289319 A1 | 10/2013 | Allgeier et al. |

FOREIGN PATENT DOCUMENTS

| | | |
|---|---|---|
| CN | 102190639 A | 9/2011 |
| DE | 4238493 C1 | 4/1994 |
| EP | 110089 B1 | 1/1988 |
| EP | 0411403 A1 | 2/1991 |
| EP | 0418925 A2 | 3/1991 |
| EP | 1243573 A1 | 9/2002 |
| EP | 1243673 A1 | 9/2002 |
| EP | 2390247 A1 | 11/2011 |
| JP | 04041449 A | 2/1992 |
| JP | 04046133 A | 2/1992 |
| JP | 2003183200 A | 7/2003 |
| JP | 2006036653 A | 2/2006 |
| JP | 04555475 B2 | 9/2010 |
| KR | 100645668 B1 | 11/2006 |
| KR | 100688765 B1 | 2/2007 |
| WO | 9955654 A1 | 11/1999 |
| WO | 2007103586 A2 | 9/2007 |
| WO | 2007103586 A3 | 9/2007 |
| WO | 2009126852 A1 | 10/2009 |
| WO | 2009133787 A1 | 11/2009 |
| WO | 2010033789 A2 | 3/2010 |
| WO | 2010033789 A3 | 3/2010 |
| WO | 2010062689 A2 | 6/2010 |
| WO | 2010099201 A1 | 9/2010 |
| WO | 2010115759 A2 | 10/2010 |
| WO | 2010115759 A3 | 10/2010 |
| WO | 2010144873 A1 | 12/2010 |
| WO | 2011149339 A1 | 12/2011 |
| WO | 2013027766 A1 | 2/2013 |
| WO | 2013066776 A1 | 5/2013 |
| WO | 2013109477 A1 | 7/2013 |

OTHER PUBLICATIONS

Abe, R. et al, "Photocatalytic overall water splitting under visible light by TaON and WO3 with an IO3-/I-shuttle redox mediator", Chem Commun, 2005, 3829-3831.

Adkins, H. et al, "The catalytic hydrogenation of organic compounds over copper chromite", J Am Chem Soc (1931), vol. 53, 1093.

Alexeev, O.S. et al, "gamma-Al2O3-Supported Pt catalysts with extremely high dispersions resulting from Pt-W interactions", J Catal, 190 (2000) 157-17.

Binder et al., "Simple chemical transformation of lignocellulosic biomass into furans for fuels and chemicals", J Am Chem Soc (2009) 131, 1979-1985.

Blanc, B. et al, "Starch-derived polyols for polymer technologies: preparation by hydrogenolysis on metal catalysts", Green Chemistry, Apr. 2000, 89-91.

Buntara, T. et al, "Caprolactam from Renewable Resources: Catalytic Conversion of 5-Hydroxymethylfurfural into Caprolactone", Angew. Chem. Int. Ed. (2011), 50(31), 7083-7087.

Buntara, T. et al., "From 5-hydroxymethylfurfural (HMF) to polymer precursors: catalyst screening studies on the conversion of 1,2,6-hexanetriol to 1,6-hexanediol", Top Catal (2012) 55, 612-619.

Caes et al., "Conversion of Fructose into 5-(Hydroxymethyl)furfural in Sulfolane", ChemSusChem, (2011), 4(3), 353-356.

Chen, K. et al, "Chemoselective hydrogenolysis of tetrahydropyran-2-methanol to 1,6-hexanediol over rhenium-modified carbon-supported rhodium catalysts", ChemCatChem (2010) 2, 547-555.

Chen, K. et al, "C-O bond hydrogenolysis of cyclic ethers with OH groups over rhenium-modified supported iridium catalysts", J Catalysis (2012) vol. 294, 171-183.

Chia, M. et al, "Selective hydrogenolysis of polyols and cyclic ethers over bifunctional surface sites on rhodium-rhenium catalysts", J Am Chem Soc (2011) vol. 133, No. 32, 12675-12680.

Connor, R. et al, "Hydrogenolysis of Oxygenated Organic Compounds", J Am Chem Soc (1932), vol. 54, 4678-4690.

Corma, A. "Inorganic Solid Acids and Their Use in Acid-Catalyzed Hydrocarbon Reactions", (1995) Chem. Rev., 95, 559-614.

Diebold, U. "The surface science of titanium dioxide", Surface Science Reports 48 (2003) 53-229.

French, G.J. et al, "A re-investigation of the thermal decomposition of ammonium paratungstate", J. Mat. Sci, 16 (1981) 3427-3436.

Gong, L. et al, "Selective hydrogenolysis of glycerol to 1,3-propanediol over a Pt/WO3/TiO2/SiO2 catalyst in aqueous media", Appl Catal A General 390 (2010) 119-126.

Gong, X.Q. et al, "Small Au and Pt Clusters at the Anatase TiO2(101) Surface: Behavior at Terraces, Steps, and Surface Oxygen Vacancies", J. Am. Chem. Soc. 130 (2008) 370-381.

Helberger et al, Justus Liebigs Annalen der Chemie (1949) 561, 215-220.

Huang, L. et al, "Direct conversion of glycerol into 1,3-propanediol over Cu-H4SiW12O40/SiO2 in vapor phase", Catal Lett, 131 (2009) 312-320.

Jae, J. et al, "Investigation into the shape selectivity of zeolite catalysts for biomass conversion", Journal of Catalysis (2011) 279, 257-268.

Jalil, P.A. et al, "A Study of Stability of Tungstophosphoric Acid, H3PW12O40, Using Synchrotron XPS, XANES, Hexane Cracking, XRD and IR Spectroscopy", J. Catalysis, 2003, 217(2), 292-297.

Jayaraman, S. et al, "Synthesis and Characterization of Pt-WO3 as Methanol Oxidation Catalysts for Fuel Cells", J Phys Chem B, 2005, 109, 22958-22966.

Jung, M.E. et al, "Synthesis of Methylene-Expanded 2',3'-Dideoxyribonucleosides", J Organic Chemistry 63 (1998) 8133-8144.

Kamalakar, G. et al, "tert-Butylation of Phenol over Ordered Solid Acid Catalysts in Supercritical Carbon Dioxide: Efficient Synthesis of 2,4-Di-tert-butylphenol and 2,4,6-Tri-tert-butylphenol", Ind Eng Chem Res, 45 (2006) 6118-6126.

Kaufmann, W.E. et al, "The use of platinum oxide as a catalyst in the reduction of organic compounds. IV. Reduction of furfural and its derivatives", J Am Chem Soc (1923) 45, 3029-3044.

Kiss, A.B. et al, "Thermal polycondensation of ammonium paratungstate, (NH4)10[W12O40(OH)2].4H2O", J. Materials Sci, 13 (1978) 2541-2547.

Koso, S. et al, "Chemoselective hydrogenolysis of tetrahydrofurfuryl alcohol to 1,5-pentanediol", Chem. Commun. (2009) 2035-2037.

Koso, S. et al, "Promoting effect of Mo on the hydrogenolysis of tetrahydrofurfuryl alcohol to 1,5-pentanediol over Rh/SiO2", J Catalysis 267 (2009), 89-92.

Kuba, S. et al, "Structure and properties of tungstated zirconia catalysts for alkane conversion", J Catalysis, 216 (2003) 353-361.

Lee, U. et al, "Structure of pentasodium trihydrogenhexatungstoplatinate(IV) icosahydrate", Acta Cryst. (1983) C39, 817-819.

(56) References Cited

OTHER PUBLICATIONS

Li, N.; Huber, G.W., "Aqueous-phase hydrodeoxygenation of sorbitol with Pt/SiO2-Al2O3: identification of reaction intermediates", Journal of Catalysis (2010) 270, 48-59.
Li, N. et al, "Renewable gasoline from aqueous phase hydrodeoxygenation of aqueous sugar solutions prepared by hydrolysis of maple wood", Green Chemistry 2011, 13, 91-101.
Liu, L. et al, "Mesoporous WO3 supported Pt catalyst for hydrogenolysis of glycerol to 1,3-propanediol", Chin. J Catal., 2012, 33, 1257-1261.
Nakagawa, Y. et al, "Heterogeneous catalysis of the glycerol hydrogenolysis", Catal Sci Technol 2011, 1, 179-190.
Nakagawa, Y. et al., "Production of 1,5-pentanediol from biomass via furfural and tetrahydrofurfuryl alcohol", Catalysis Today 195 (2012) 136-143.
Nikolla, E. et al., "'One-Pot' Synthesis of 5-(Hydroxymethyl)furfural from Carbohydrates Using Tin-Beta Zeolite", ACS Catal. (2011), 1, 408-410.
Okuhara, T. et al, "Insoluble heteropoly compounds as highly active catalysts for liquid-phase reactions", J. Mol. Catal. 74 (1992) 247-256.
Ott, L. et al, "Catalytic Dehydration of Glycerol in sub- and supercritical water: a new chemical process for acrolein production", Green Chemistry, 2006, pp. 214-220, vol. 8.
Pae, Y.I. et al, "Characterization of NiO-TiO2 modified with WO3 and catalytic activity for acid catalysis", Bull. Korean Chem. Soc. 2004, vol. 25(12), 1881-1888.
Roman-Leshkov, Y. et al., "Solvent effects on fructose dehydration to 5-hydroxymethylfurfural in biphasic systems saturated with inorganic salts", Top Catal (2009) 52:297-303.
SRI Process Economics Program, 31, Hexamethylenediamine Nov. 1967.
Ten Dam, J. et al, "Pt/Al2O3 catalyzed 1,3-propanediol formation from glycerol using tungsten additives", ChemCatChem (2013), 5(2), 497-505.
Tong, X. et al, "Biomass into chemicals: conversion of sugars to furan derivatives by catalytic processes", Appl. Catalysis A General, 385 (2010) 1-13.
Tripathy, P.K. et al, "A comparative study on the thermal decomposition of ammonium p-tungstate in batch and fluidized-bed reactors", Ind Eng Chem Res 36 (1997) 3602-3606.
Trost, B. M. "Cyclizations Made Easy by Transition Metal Catalysts", in Homogeneous Transition Metal Catalyzed Reactions; Moser, W. et al; Adv. Chem. 31, 1992, ACS, Washington, DC.
Xu, W. et al, "Direct catalytic conversion of furfural to 1,5-pentanediol by hydrogenolysis of the furan ring under mild conditions over Pt/Co2AlO4 catalyst" Chem Comm, Royal Society of Chemistry (2011) vol. 47, No. 13, 3924-3926.
Yamazoe, S. et al, "XAFS Study of Tungsten L1-, L3-Edges: Structural Analysis of Loaded Tungsten Oxide Species", Envir Sci, Research Frontiers 2008, Spring 8, 138-139.
Yamazoe, S. et al, "XAFS Study of Tungsten L1- and L3-Edges: Structural Analysis of WO3 Species Loaded on TiO2 as a Catalyst for Photo-oxidation of NH3", J. Phys Chem C 2008, 112, 6869-6879.
Yoshinaga, Y. et al, "Shape-selective oxidation catalysed by a Pt-promoted ultramicroporous heteropoly compound", J.Chem. Soc. Faraday Trans 1998, 94(15) 2235-2240.
Zanardi, M.M. et al, "Synthesis of a simple chiral auxiliary derived from levoglucosenone and its application in a Diels-Alder reaction", Tetrahedron letters 50 (2009) 999-1002.
Database CAPLUS on STN, AN 1979:151575, Nishino et al, JP 53149905 A, Dec. 27, 1978 (abstract).
Database WPIX on STN, AN 1979-11181B [197906], Nishino et al, JP53149905 A Dec. 27, 1978 (abstract).
Office action dated Apr. 9, 2014 for copending U.S. Appl. No. 13/870,080.
Notice of allowance dated Mar. 11, 2014 for copending U.S. Appl. No. 13/870,091.
Notice of allowance dated Mar. 26, 2014 for copending U.S. Appl. No. 13/870,072.
U.S. Appl. No. 13/870,095, filed Apr. 25, 2013.
Efremov, A.A. et al, "Conversions of Levoglucosenone in Acid Media", Sibirskii Khimicheskii Zhurnal, 1992, 6, 34-39 Translation.
Office actions dated Sep. 27, 2013 and Dec. 17, 2013 for copending U.S. Appl. No. 13/729,464.
Notice of allowance dated Oct. 1, 2013 for copending U.S. Appl. No. 13/729,494.
Notice of allowance dated Nov. 19, 2013 for copending U.S. Appl. No. 13/729,401.
Office action dated Dec. 20, 2013 for this U.S. Appl. No. 13/729,507.
Notice of allowance dated Jan. 13, 2014 for copending U.S. Appl. No. 13/729,494.
U.S. Appl. No. 14/031,356, filed Sep. 19, 2013.
U.S. Appl. No. 61/782,172, filed Mar. 14, 2013.
U.S. Appl. No. 61/782,198, filed Mar. 14, 2013.
Office action dated Feb. 27, 2014 for copending U.S. Appl. No. 13/870,095.
Office action dated Feb. 27, 2014 for copending U.S. Appl. No. 13/870,099.
Alamillo, R. et al., "Selective Hydrogenation of Biomass-Derived 5-Hydroxymethylfurfural Using Heterogeneous Catalysts", Green Chem., 2012, 14, 1413.
Jung, K.J. et al., "Furfural Decarbonylation Catalyzed by Charcoal Supported Palladium: Part I—Kinetics", Biomass 16 (1988) 63-76.
Jung, K.J. et al., "Furfural Decarbonylation Catalyzed by Charcoal Supported Palladium: Part II—A Continuous Process", Biomass 16 (1988) 89-96.
Lichtenthaler, F.W. "Carbohydrates as Organic Raw Materials" 2010 Wiley-VCH Verlag GmbH&Co. KGaA, Weinheim 10.1002/14356007.n05_n07.
Qin, L.-Z. et al., "Aqueous-phase deoxygenation of glycerol to 1,3-propanediol over Pt/WO3/ZrO2 catalysts in a fixed-bed reactor", Green Chem., 2010, 12, 1466-1472.
Rao, R.S. et al., "Furfural Hydrogenation Over Carbon-Supported Copper", Catalysis Letters 60 (1999) 51-57.
Zheng, H.-Y. et al., "Towards Understanding the Reaction Pathway in Vapour Phase Hydrogenation of Furfural to 2-Methylfuran", J Molecular Catalysis A: Chemical 246 (2006) 18-23.
International Search Report dated May 6, 2014, PCT/US2012/062314.
Copending application No. PCT/US14/23874 filed Mar. 12, 2014.
Copending application No. PCT/US14/23905 filed Mar. 12, 2014.
Notice of allowance dated Apr. 25, 2014 for copending U.S. Appl. No. 13/729,464.
Notice of allowance dated Apr. 28, 2014 for copending U.S. Appl. No. 13/729,494.
Office action dated May 7, 2014 for copending U.S. Appl. No. 13/729,390.
Notice of allowance dated Jun. 10, 2014 for copending U.S. Appl. No. 13/870,091.
Notice of allowance dated Jun. 23, 2014 for copending U.S. Appl. No. 13/870,072.
U.S. Appl. No. 13/870,095, (2014).
International Search Report dated Mar. 29, 2013, PCT/US2012/062314.
International Search Report dated Apr. 29, 2013, PCT/US2012/071891.
International Search Report dated Apr. 29, 2013, PCT/US2012/071907.
International Search Report dated Apr. 29, 2013, PCT/US2012/071893.
International Search Report dated Apr. 29, 2013, PCT/US2012/071912.
International Search Report dated Jul. 26, 2013, PCT/US2013/038403.
International Search Report dated Jul. 18, 2013, PCT/US2013/038418.
International Search Report dated Jul. 24, 2013, PCT/US2013/038441.
International Search Report dated Jul. 24, 2013, PCT/US2013/038436.

(56) References Cited

OTHER PUBLICATIONS

Office actions dated Jun. 26, 2013 and Sep. 13, 2013 for copending U.S. Appl. No. 13/729,390, (2014).
Efremov ChemistryOfNatComds 35 5 582-589__1999.
Efremov Intl Symp Wood Pulping Chemstry 1995 689.
Efremov Sibirskii Khimicheskii Zhurnal 92 6 34-39, (1992).
Fogler Elements of Chemical Reaction Engineering, 2nd Edition, Prentice-Hall (1992) (Book).
International Search Report Dated Apr. 30, 2013, PCT/US2012/071894.
Karinen Etal Chem Sus Chem 2011 4 1002-1016.
Miftakhov et al Russian Chemical Reviews 63(10) 869-882 (1994).
Ponder Applied Biochemistry and Biotechnology vol. 24/25, 41-47 1990.
Shafizadeh Etal Carobhydrate Res 71 1979 169-191.

PRODUCTION OF HYDROXYMETHYLFURFURAL FROM LEVOGLUCOSENONE

This application claims priority under 35 U.S.C. §119(e) from, and claims the benefit of, U.S. Provisional Application No. 61/582,067, filed Dec. 30, 2011, which is by this reference incorporated in its entirety as a part hereof for all purposes.

FIELD OF DISCLOSURE

The present invention relates to processes for preparing 5-hydroxymethyl-2-furfural from levoglucosenone.

BACKGROUND

Industrial chemicals obtained from inexpensive sources are desirable for use in industrial processes, for example as raw materials, solvents, or starting materials. It has become increasingly desirable to obtain industrial chemicals or their precursors from materials that are not only inexpensive but also benign in the environment. Of particular interest are materials which can be obtained from renewable sources, that is, materials that are produced by a biological activity such as planting, farming, or harvesting. As used herein, the terms "renewable" and "biosourced" can be used interchangeably.

Furan and its derivatives, particularly $C_5$ and $C_6$ furanic compounds such as furfural and 5-hydroxymethyl-2-furfural (HMF, also known as 5-hydroxymethyl-2-furaldehyde), are useful intermediates in the production of fuels and industrial chemicals for use as pharmaceuticals, herbicides, stabilizers, and polymers. For example, HMF can be a useful material for the synthesis of tetrahydrofuran 2,5-dimethanol and 1,6-hexanediol. For cost and environmental reasons, it would desirable to be able to synthesize such compounds from biomass. However, the synthesis of intermediates from biomass often relies on edible feedstock materials. For example, many routes that rely on dehydration of $C_6$ carbohydrates to $C_5$ and $C_6$ furanic materials, such as furfural and HMF, start with glucose and fructose as a feedstock (see R. Karinen et al., *ChemSusChem*, 4(8), (2011), 1002-1016).

At the highly acidic aqueous environments and high temperatures needed to form HMF from lignocellulose, HMF exhibits a high rate of decomposition to levulinic acid, formic acid, and a significant amount of humin byproducts which are undesirable tar-like materials. A process which allows for the production of HMF in water under close to neutral conditions from a non-food biomass lignocellulose derived material would be highly desirable.

Levoglucosenone, an isomer of HMF, can be produced from woody (lignocellulosic) material through pyrolysis. F. Shafizadeh et al. (*Carbohydrate Research*, 71, (1979), 169-191) found that heating levoglucosenone in 0.5 M HCl (pH=0.3) in a boiling water bath to reaction completion (2.5 hours) produced HMF in a 16% yield. Heating levoglucosenone in 2 M acetic acid (pH=2.2) produced 1,6-anhydro-3-deoxy-β-D-erythro-hexopyranos-2-ulose, (represented by Formula (I-a)) in a 77% yield, but no HMF.

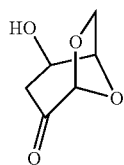

I-a

There remains a need for a route to furanic compounds, such as 5-hydroxymethyl-2-furfural, from non-food biomass-derived compounds such as levoglucosenone that avoids the production of undesired reactive intermediates.

SUMMARY

Described herein are processes to convert levoglucosenone to a product mixture comprising 5-hydroxymethyl-2-furfural. Such a product mixture can be heated in the presence of hydrogen and a hydrogenation catalyst to form a subsequent product mixture comprising 1,6-hexanediol and/or chemical intermediates which are useful in the synthesis of 1,6-hexanediol.

In one embodiment, a process is disclosed comprising:

a) contacting an aqueous reaction mixture comprising levoglucosenone with a catalyst, wherein the initial pH of the reaction mixture is between about 3 and about 6, and b) heating the reaction mixture at a temperature between about 120° C. and about 200° C. at a pressure of ambient pressure to about 1000 psi for a time sufficient to form a product mixture comprising 5-hydroxymethyl-2-furfural.

In one embodiment, the process further comprises:

c) heating the product mixture comprising 5-hydroxymethyl-2-furfural in the presence of hydrogen and a first hydrogenation catalyst at a temperature between about ambient temperature and about 120° C. at a pressure of about ambient pressure to about 1000 psi to form a second product mixture comprising one or more of 2,5-furandimethanol and tetrahydrofuran-2,5-dimethanol;

d) separating the second product mixture from the first hydrogenation catalyst; and e) reacting the second product mixture with hydrogen in the presence of a second hydrogenation catalyst at a temperature between about 120° C. and about 260° C. at a pressure of about 800 psi to about 2000 psi to form a third product mixture comprising one or more of 1,2,6-hexanetriol, 2-hydroxymethyltetrahydropyran, and 1,6-hexanediol.

In another embodiment, the process further comprises:

c) heating the product mixture comprising 5-hydroxymethyl-2-furfural in the presence of hydrogen and a hydrogenation catalyst at a temperature between about ambient temperature and 120° C. at a pressure of about ambient pressure to about 1000 psi for a time period of 10 minutes to 10 hours, and then at a temperature between about 120° C. and about 260° C. at a pressure of 800 psi to about 2000 psi for a sufficient time to form a second product mixture comprising one or more of 1,2,6-hexanetriol, 2-hydroxymethyltetrahydropyran, and 1,6-hexanediol.

DETAILED DESCRIPTION

The methods described herein are described with reference to the following terms.

As used herein, where the indefinite article "a" or "an" is used with respect to a statement or description of the presence of a step in a process of this invention, it is to be understood, unless the statement or description explicitly provides to the contrary, that the use of such indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about," the claims include equivalents to the quantities. The term "about" may mean within 10% of the reported numerical value, preferably within 5% of the reported numerical value.

As used herein, the term "biomass" refers to any hemicellulosic or lignocellulosic material and includes materials comprising hemicellulose, and optionally further comprising cellulose, lignin, starch, oligosaccharides and/or monosaccharides.

As used herein, the term "lignocellulosic" means comprising both lignin and cellulose. Lignocellulosic material may also comprise hemicellulose. In some embodiments, lignocellulosic material contains glucan and xylan.

Hemicellulose is a non-cellulosic polysaccharide found in lignocellulosic biomass. Hemicellulose is a branched heteropolymer consisting of different sugar monomers. It typically comprises from 500 to 3000 sugar monomeric units.

Lignin is a complex high molecular weight polymer and can comprise guaiacyl units as in softwood lignin, or a mixture of guaiacyl and syringyl units as in hardwood lignin. As used herein, the abbreviations "Lgone" and "LGone" refer to levoglucosenone, also known as 1,6-anhydro-3,4-dideoxy-β-D-pyranosen-2-one. The chemical structure of levoglucosenone is represented by Formula (I).

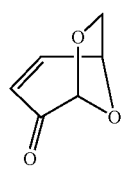

I

As used herein, the abbreviation "HMF" refers to 5-hydroxymethyl-2-furfural, also known as 5-hydroxymethyl-2-furaldehyde and as 5-(hydroxymethyl)furfural. The chemical structure of 5-hydroxymethyl-2-furfural is represented by Formula (II).

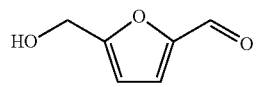

II

As used herein, the abbreviation "FDM" refers to 2,5-furandimethanol, also known as 2,5-bis(hydroxymethyl)furan. The chemical structure of 2,5-furandimethanol is represented by Formula (III).

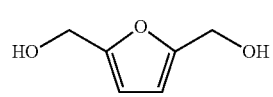

III

As used herein, the abbreviation "THFDM" refers to tetrahydro-2,5-furandimethanol (also known as tetrahydrofuran-2,5-dimethanol or 2,5-tetrahydrofurandimethanol, or 2,5-bis[hydroxymethyl]tetrahydrofuran) and includes a mixture of stereoisomers (cis and racemic trans isomers). The chemical structure of tetrahydro-2,5-furandimethanol is represented by Formula (V).

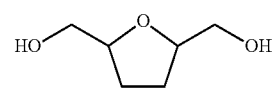

V

As used herein, the abbreviation "1,2,6-HT" refers to 1,2,6-hexanetriol and includes a racemic mixture of isomers. The chemical structure of 1,2,6-hexanetriol is represented by Formula (VI).

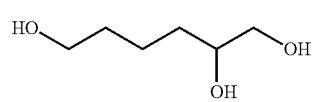

VI

As used herein, the abbreviation "THPM" refers to tetrahydro-2H-pyran-2-methanol, also known as 2-hydroxymethyltetrahydropyran, and includes a racemic mixture of isomers. The chemical structure of tetrahydro-2H-pyran-2-methanol is represented by Formula (VII).

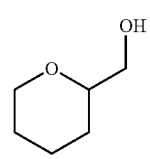

VII

As used herein, the abbreviation "1,6-HD" refers to 1,6-hexanediol. The chemical structure of 1,6-hexanediol is represented by Formula (IX).

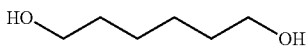

As used herein, the abbreviation "1,2-HD" refers to 1,2-hexanediol and includes a racemic mixture of isomers. The chemical structure of 1,2-hexanediol is represented by Formula (X).

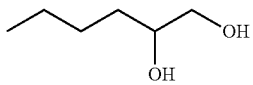

As used herein, the abbreviation "1,5-HD" refers to 1,5-hexanediol and includes a racemic mixture of isomers. The chemical structure of 1,5-hexanediol is represented by Formula (XII).

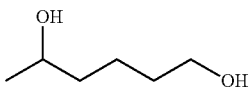

As used herein, the abbreviation "1,5PD" refers to 1,5-pentanediol. The chemical structure of 1,5-pentanediol is represented by Formula (XIII).

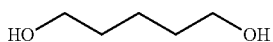

Disclosed herein are processes for obtaining 5-hydroxymethyl-2-furfural from levoglucosenone, which in turn can be derived from a renewable biosource. As used herein, the term "renewable biosource" includes biomass and animal or vegetable fats or oils.

A renewable biosource can be pyrolyzed under high temperature conditions in the presence of an acid catalyst to provide useful chemical intermediates. For example, pyrolysis of wood, starch, glucose or cellulose can produce levoglucosenone by known and conventional methods (see, for example, Ponder (*Applied Biochemistry and Biotechnology*, Vol 24/25, 41-41 (1990)) or Shafizadeh (*Carbohydrate Research,* 71, 169-191 (1979)).

In the processes disclosed herein, a catalyst is contacted with an aqueous reaction mixture comprising levoglucosenone, wherein the initial pH of the reaction mixture is between about 3 and about 6, and then heated at reaction conditions sufficient to effect formation of a product mixture comprising 5-hydroxymethyl-2-furfural.

The concentration of levoglucosenone in water, whether dissolved or as a suspension, is between about 1 wt % and about 50 wt %; in some embodiments it is between and optionally includes any two of the following values: 1 wt %, 5 wt %, 10 wt %, 15 wt %, 20 wt %, 25 wt %, 30 wt %, 35 wt %, 40 wt %, 45 wt %, and 50 wt %. The optimal concentration will depend on the intended reaction conditions.

The pH of the reaction mixture is between about 3 and about 6. In some embodiments the pH is between and optionally includes any two of the following values: 3, 4, 5, and 6. In some embodiments, levoglucosenone as obtained by pyrolysis of biomass contains small amounts of acidic components, including formic acid, acetic acid, and levulinic acid.

The catalyst can be homogeneous or heterogeneous. In some embodiments the catalyst is an acid. Examples of catalysts include without limitation: mineral acids such as, for example, $H_2SO_4$, HCl, $H_3PO_4$, and $HNO_3$; organic acids, such as propionic acid, glycolic acid, benzoic acid, and levulinic acid; zeolites, such as H-Y zeolite, mordenite, faujasite and beta zeolite; aluminosilicates such as mesoporous silica; montmorillonites, and derivatives thereof; heteropolyacids such as 12-tungstophosphoric acid and derivatives thereof; acidic resins, such as ion-exchange resins containing sulfonic acid or carboxylic acid functional groups; metal oxides such as tungsten(IV) oxide, tungsten(VI) oxide, molybdenum(IV) oxide, molybdenum(VI) oxide, rhenium (IV) oxide, rhenium(VII) oxide, ammonium perrhenate ($NH_4ReO_4$), and aluminum oxide; and supported transition metal catalysts, such as $PtWO_x/TiO_2$, and $PdMoO_x/TiO_2$.

In some embodiments, the catalyst loading is determined by the amount of acid catalyst needed to achieve the desired pH, that is, between about pH 3 and about pH 6. In some embodiments, the catalyst loading can be from about 0.1 wt % to about 20 wt %, for example from about 0.2 wt % to about 15 wt %, or from about 0.2 wt % to about 10 wt %, based on the weight of the water.

An inert gas sweep (e.g., nitrogen) can be used to exclude oxygen from the reaction vessel. The applied pressure of the inert gas during the reaction can range from ambient pressure (i.e., 0 applied pressure) to about 1000 psi. In some embodiments, the applied pressure is between and optionally includes any two of the following values: 0, 50, 100, 200, 300, 400, 500, 600, 700, 800, 900, and 1000 psi.

The reaction temperature is between about 100° C. and about 200° C. In an embodiment, the reaction temperature is between about 120° C. and about 150° C., or between about 120° C. and about 200° C. In some embodiments, the reaction temperature is between and optionally includes any two of the following values: 100° C., 110° C., 120° C., 130° C., 140° C., 150° C., 160° C., 170° C., 180° C., 190° C., and 200° C.

The processes disclosed herein can be carried out in standard reactors as are known in the art, such as a batch reactor, continuous stirred tank reactor, or a continuous flow reactor. In one embodiment, the continuous flow reactor is in liquid flow mode. The suitable vessel can be equipped with a means, such as impellers, for agitating the reaction mixture. These and other suitable reactors are more particularly described, for example, in Fogler, *Elements of Chemical Reaction Engineering*, $2^{nd}$ edition, Prentice-Hall, Inc., (1992).

At the end of the designated heating time, the catalyst can be separated from the product mixture by methods known in the art, for example, by filtration. After separation from the catalyst, the product mixture components, including 5-hydroxymethyl-2-furfural and any unreacted levoglucosenone, can be separated from one another using any appropriate method known in the art, for example distillation, extraction, chromatography, adsorption by resins, separation by molecular sieves, or pervaporation.

In one embodiment, the process further comprises:

c) heating the product mixture comprising 5-hydroxymethyl-2-furfural in the presence of hydrogen and a first hydrogenation catalyst at a temperature between about ambient temperature and about 120° C. at a pressure of about ambient pressure to about 1000 psi to form a second product mixture comprising one or more of 2,5-furandimethanol and tetrahydrofuran-2,5-dimethanol;

d) separating the second product mixture from the first hydrogenation catalyst; and e) reacting the second product mixture with hydrogen in the presence of a second hydrogenation catalyst at a temperature between about 120° C. and about 260° C. at a pressure of about 800 psi to about 2000 psi to form a third product mixture comprising one or more of 1,2,6-hexanetriol; 2-hydroxymethyltetrahydropyran; and 1,6-hexanediol.

In one embodiment, the process further comprises:

c) heating the product mixture comprising 5-hydroxymethyl-2-furfural in the presence of hydrogen and a hydrogenation catalyst at a temperature between about ambient temperature and 120° C. at a pressure of about ambient pressure to about 1000 psi for a time period of 10 minutes to 10 hours, and then at a temperature between about 120° C. and about 260° C. at a pressure of 800 psi to about 2000 psi for a sufficient time to form a second product mixture comprising one or more of 1,2,6-hexanetriol; 2-hydroxymethyltetrahydropyran; and 1,6-hexanediol.

In one embodiment, the second product mixture comprises 1,6-hexanediol.

Suitable hydrogenation catalysts for this reaction step include one or more of copper catalysts, supported platinum/tungsten catalysts, supported platinum catalysts, and supported palladium catalysts, supported ruthenium catalysts, supported rhodium catalysts, supported nickel catalysts, catalysts derived from nickel-aluminum alloys, and catalysts derived from cobalt-aluminum alloys.

2,5-Furandimethanol, tetrahydrofuran-2,5-dimethanol, 1,2,6-hexanetriol, and 2-hydroxymethyltetrahydropyran are intermediates useful in the production of 1,6-hexanediol. 1,6-Hexanediol is a useful intermediate in the industrial preparation of nylon. For example, 1,6-hexandiol can be converted by known methods to 1,6-hexamethylene diamine, a useful monomer in nylon production.

EXAMPLES

The methods described herein are illustrated in the following examples. From the above discussion and these examples, one skilled in the art can ascertain the essential characteristics of this invention, and without departing from the spirit and scope thereof, can make various changes and modifications of the invention to adapt it to various uses and conditions.

The meaning of abbreviations is as follows: "g" means gram(s), "GC" means gas chromatography, "HPLC" means high pressure liquid chromatography, "h" means hour(s), "mL" means milliliter(s), "psi" means pound(s) per square inch, "wt %" means weight percentage, "μm" means micrometer(s), "%" means percent, "° C." means degrees Celcius, "mg" means milligram(s), "mm" means millimeter(s), "mL/min" means milliliters per minute, "m" means meter(s), "μL" means microliter(s), "mmol" means millimole(s), "min" means minute(s), "mol %" means mole percent, "M" means molar, "mg/g" means milligram(s) per gram, "RPM" means revolutions per minute, "MPa" means megaPascal(s), "Ex" means example, and "Comp Ex" means Comparative Example.

Materials

All reagents were obtained from Sigma-Aldrich (St. Louis, Mo.) unless stated otherwise. Levoglucosenone (90% purity) was obtained from TimTec LLC (Newark, Del.). CBV 712 H-Y (6), CBV 780 H-Y (40), CBV 901 H-Y (80), and CBV 21A H-mordenite (10) were obtained from Zeolyst International (Conshohocken, Pa.) and calcined at 550° C. in air for 8 h before use. The sponge nickel catalyst (A-2000) was obtained from Johnson Matthey Catalysts (West Deptford, N.J.) and the activated nickel catalyst (BLM 112 W) was obtained from Evonik Degussa Corporation (Parsippany, N.J.). The sulfonic acid-based cation exchange resin used was DOWEX™ 50WX8, 200-400 mesh, which was obtained from Sigma-Aldrich. The $Al_2O_3$ (acidic, Brockmann I activated standard grade) was purchased from Sigma-Aldrich. Tetrahydro-2,5-furandimethanol (95%) and 2,5-furandimethanol (95%) were purchased from Penn A Kem (Memphis, Tenn.). Tetrahydrofuran was obtained from EMD Chemicals (Gibbstown, N.J.). Deionized water (pH=5.2) was used unless otherwise indicated.

The $H_{0.5}Cs_{2.5}PW_{12}O_{40}$ catalyst was prepared from aqueous solutions of $H_3PW_{12}O_{40}$ and $Cs_2CO_3$. The $H_3PW_{12}O_{40}$ was dehydrated at 60° C. for 2 h prior to use and the $Cs_2CO_3$ was dehydrated at 420° C. for 2 h prior to use. The heteropolyacid was prepared by titrating an aqueous solution of $H_3PW_{12}O_{40}$ (0.08 M) with an aqueous solution of $Cs_2CO_3$ (0.25 M) at room temperature at a rate of 1 mL/min. The white colloidal suspension was evaporated to a solid at 50° C. under vacuum and then placed in a 120° C. vacuum oven for 2 h. The solids were then treated at 300° C. for 1 h.

The $Pt/W/TiO_2$ catalyst was synthesized using the following procedure. Aerolyst 7708 $TiO_2$ (0.92 g, Evonik) that had been ground with a mortar and pestle and passed through a 0.0165" mesh sieve, then wetted with 1.0 mL of deionized water, was impregnated with 0.08 g of tetraammineplatinum (II) nitrate (Strem, Cat #78-2010) dissolved in 1.0 mL of deionized water. The resulting wet suspension was vortexed for 15 min and then vacuum-dried at 110° C. overnight. The resulting precipitate was wetted with 1.0 mL of deionized water. Then 0.0535 g of ammonium tungsten oxide hydrate (para analogue) (Alfa, stock #22640), which had been thoroughly dissolved in 2.0 mL of deionized water, was added on to the wetted precipitate. The resulting wet suspension was vortexed for 15 min and then vacuum-dried at 110° C. overnight. After reaching room temperature, the material was transferred to a ceramic boat and calcined in air at 400° C. for three h. The calcined $Pt/W/TiO_2$ catalyst had a Pt loading of 4 wt % based on the total weight of the catalyst, and a 1:1 molar ratio of Pt:W.

The $Pd/Mo/TiO_2$ catalyst synthesis was similar except palladium (II) nitrate dihydrate (Aldrich, Cat. #76070) and ammonium molybdate hydrate (para analogue) (Alfa, stock #10811) were used. The calcined $Pd/Mo/TiO_2$ catalyst had a Pd loading of 4 wt % based on the total weight of the catalyst, and a 1:1 molar ratio of Pd:Mo.

Methods

Sample Preparation and Reaction Conditions for an 8-Well Parallel Pressure Reactor Into 1.5 mL glass vials (ROBO Autosampler Vial, VWR International, Radnor, Pa.), LGone (37.5 mg, 5 wt % loading) was introduced, followed by water (0.75 g) and catalyst. A magnetic stirbar (7×2 mm, VWR International) was inserted and the vials capped with a perforated septum to limit vapor transfer rates. The vials were then placed into a stainless steel (SS316) parallel pressure reactor (8 individual wells) and sealed. Any unused wells were filled with water. Upon sealing, the reactor was connected to a high pressure gas manifold and the content was purged with nitrogen gas (1000 psi) 3 times before pressurizing. The reactor was then heated to the desired reaction temperature and left for a specified time. Upon cooling, the reactor was depressurized, the vials removed and prepared for analysis.

Sample Preparation and Reaction Conditions for a 1-well Pressure Reactor

Into a stainless steel (SS316) pressure reactor containing 1 well, was placed LGone, water, and the desired catalyst. A magnetic stirbar (7×2 mm, VWR International) was inserted and the reactor block was sealed. Upon sealing, the reactor was connected to a high pressure gas manifold and the content was purged with nitrogen gas (1000 psi) 3 times before pressurizing. The reactor was then heated to the desired reaction temperature and left for the specified time. Upon cooling, the block was depressurized and the reaction contents collected for analysis.

Measurement of pH

The initial pH of the reaction samples was measured using pH strips (colorpHast®, EMD, Billerica, Mass.), or with a pH meter (Beckman φ340 pH/Temp Meter). When using the strips to measure pH, the pH values were recorded as a single numerical value (for example, 4) or a range of values (for example, 3-4). When using the pH meter, the pH values were recorded up to two decimal places (for example, 3.00). The initial pH of the samples before reaction was recorded. The pH of deionized water measured with the pH strips was 5 and with the pH meter was 5.2. The pH of deionized water and 5 wt % levoglucosenone was 5.4.

GC Analysis

To each cooled glass vial containing a reaction product mixture, an internal standard solution of 3.5% diethyleneglycol diethyl ether in isopropanol was added to approximately double the original volume. The sample was mixed thoroughly and 1 mL was filtered through a 0.2 μm filter (GHP Acrodisc 13 mm syringe filter, PALL Life Sciences, Port Washington, N.Y.) into an autosampler vial. The sample analysis was performed with an Agilent 5890 gas chromatograph with 7673 autosampler. The column was an Agilent RTX Stabilwax column (30 m×0.25 mm×0.5 μm). The injector was maintained at 250° C. and the injection volume was 1 μL with a split ratio of 20:1. The carrier gas was helium at 1 mL/min and a FID detector at 250° C. was used. Concentrations were determined from a standard calibration curve developed for each of the analytes with diethylene glycol diethyl ether.

HPLC Analysis

Each cooled reaction sample was transferred to a glass vial and diluted with water to a mass of 14-20 g. One gram of the diluted reaction sample was then added to a second glass vial. To this second vial was added one gram of 2-hexanol in distilled water (5 mg/g) as the internal standard. A solution of 1% sodium bicarbonate in water was also added to the vial to bring the sample weight up to 5 g. The sample was mixed thoroughly and 1 mL was then filtered through a 0.2 μm filter (GHP Acrodisc 13 mm syringe filter, PALL Life Sciences, Port Washington, N.Y.). The concentration of HMF, FDM, and THFDM were measured by HPLC (1200 Series, Agilent Technologies, Santa Clara, Calif.) using an Aminex HPX-87P column (300 mm×7.8 mm, Bio-Rad Laboratories, Hercules, Calif.) fitted with a guard column and detected using a RI detector. The column and guard column were held at 80° C. and the RI Detector was held at 55° C. Injection volume was 20 μL and sample run times were 60 min in length with a 0.6 mL/min flow rate using a water mobile phase. Concentrations were determined from a standard calibration curve developed for each of the analytes with 2-hexanol. Using this HPLC method, retention time of HMF was 32.9 min, 22.9 min for FDM, and 41.8 min for THFDM.

Example 1

Conversion of Levoglucosenone to HMF in Water at pH 5

The reaction was prepared as described above using a 1-well pressure reactor. The LGone (5 wt % loading) was added to water for a total weight of 15 g and heated at 60° C. for 2 h and increased to 180° C. for an additional 4 h under 850 psi nitrogen. The initial pH was 5. It is believed that this is due to the pH of the deionized water and/or any acidic impurities present in the LGone. After cooling, the reaction mixture was analyzed and revealed no starting material and 25% HMF yield.

Examples 2-25

Conversion of Levoglucosenone to HMF in Water with Selected Catalysts

These samples were run in the 8-well pressure reactor as described above, at 150° C. for 4 h while pressurized at 850 psi nitrogen. The results in Table 1 show that HMF was formed from LGone in the presence of a variety of homogeneous and heterogeneous catalysts. The heterogeneous catalysts were used as received and the zeolites were used as powders.

TABLE 1

Results for Examples 2-25

| Ex | Catalyst | Loading (mg) | Initial pH | LGone Conversion (%) | HMF Yield (%) |
|---|---|---|---|---|---|
| 2 | None | 0 | 5 | 69 | 12 |
| 3 | Sulfonic acid cation exchange resin DOWEX ™ (50WX8-400) | 30 | 3-4 | 94 | 65 |
| 4 | H-Y (Si/Al = 6) * | 50 | 4-5 | 94 | 38 |
| 5 | H-Y (Si/Al = 40) | 50 | 3-4 | 94 | 54 |
| 6 | H-Y (Si/Al = 80) | 30 | 4 | 93 | 42 |
| 7 | H-mordenite (Si/Al = 10) | 30 | 4 | 99 | 47 |
| 8 | Montmorillonite K 10 | 50 | 3.5 | 91 | 43 |
| 9 | Phosphotungstic acid hydrate | 2 | 3.0 | 84 | 47 |
| 10 | $H_{0.5}Cs_{2.5}PW_{12}O_{40}$ | 2 | 4 | 79 | 30 |
| 11 | Tungstic acid ($H_2WO_4$) | 50 | 3.5 | 88 | 51 |
| 12 | Tungsten(VI) oxide | 60 | 4 | 86 | 30 |
| 13 | Molybdenum(IV) oxide | 30 | 4 | 74 | 15 |
| 14 | Molybdenum(VI) oxide* | 50 | 3-4 | 92 | 40 |
| 15 | Aluminum oxide (acidic) * | 31 | 4 | 71 | 20 |
| 16 | Rhenium(IV) oxide | 10 | 3.0 | 71 | 18 |
| 17 | Ammonium perrhenate* ($NH_4ReO_4$) | 34 | 5-6 | 89 | 30 |
| 18 | $PtW/TiO_2$* | 40 | 5-6 | 79 | 29 |
| 19 | $PdMo/TiO_2$* | 40 | 5 | 72 | 34 |
| 20 | Glycolic acid | 25 | 3 | 98 | 35 |
| 21 | Levulinic acid | 20 | 3 | 86 | 37 |
| 22 | Benzoic acid | 3 | 3 | 100 | 25 |
| 23 | Propionic acid | 5.4 | 3.1 | 61 | 27 |
| 24 | $H_2SO_4$ (0.005 M) | 58.7 | 3.6 | 58 | 36 |
| 25 | $H_3PO_4$ (0.025 M) | 39.8 | 3.5 | 52 | 43 |

* These examples used autogenous pressure under $N_2$ atmosphere.

Example 26

Conversion of Levoglucosenone to HMF with H-Y as Catalyst

The reaction was prepared as described above using a 1-well pressure reactor. The LGone (0.23 g, 5 wt % loading)

and H-Y (40) catalyst (148 mg) were added to water (4.5 g) for a total weight of 4.9 g and heated at 180° C. for 4 h under 850 psi nitrogen. The initial pH was 4. After cooling, the reaction mixture was analyzed and revealed 92% LGone conversion and 21% HMF yield.

Example 27

Conversion of Levoglucosenone to HMF Under Autogenous Pressure

The reaction was performed in an 8-well pressure reactor as described above at 150° C. for 4 h with autogenous pressure or at 850 psi nitrogen with a catalyst. As shown in Table 2, HMF was formed with or without added pressure. Results for Example 5 are included.

TABLE 2

Results for Examples 5 and 27

| Ex | Catalyst | Loading (mg) | pH | $N_2$ Pressure (psi) | Lgone Conversion (%) | HMF Yield (%) |
|---|---|---|---|---|---|---|
| 27 | H-Y (Si/Al = 40) CBV-780 | 50 | 3-4 | 0 | 96 | 50 |
| 5 | H-Y (Si/Al = 40) CBV-780 | 50 | 3-4 | 850 | 94 | 54 |

Examples 28-33

Conversion of Levoglucosenone to HMF at 120° C. and 150° C.

The reaction was performed in an 8-well pressure reactor as described above with different catalysts. The results are shown in Table 3 and illustrate that the temperature can be varied to improve HMF yield for a given set of conditions. For example, using phosphotungstic acid as the catalyst (2 mg, 4 h run time), increasing the reaction temperature from 120° C. to 150° C. improved the yield of HMF from 3% to 47%.

TABLE 3

Results for Examples 28-33

| Ex | Catalyst | Loading (mg) | pH | Temp. (° C.) | Time (h) | Lgone Conversion (%) | HMF Yield (%) |
|---|---|---|---|---|---|---|---|
| 28 | DOWEX ™ (50WX8-400)sulfonic acid cation exchange resin | 15 | 3-4 | 120 | 1 | 72 | 21 |
| 29 | DOWEX ™ (50WX8-400)sulfonic acid cation exchange resin | 15 | 3-4 | 150 | 1 | 99 | 45 |
| 30 | Phosphotungstic acid hydrate | 2 | 3.0 | 120 | 4 | 66 | 3 |
| 31 | Phosphotungstic acid hydrate | 2 | 3.0 | 150 | 4 | 100 | 47 |
| 32 | H-Y (Si/Al = 40) CBV-780 | 50 | 3-4 | 120 | 1 | 74 | 12 |
| 33 | H-Y (Si/Al = 40) CBV-780 | 50 | 3-4 | 150 | 1 | 99 | 45 |

Examples 34-35

Conversion of Levoglucosenone to HMF with Different Reaction Times

The reaction was performed in an 8-well pressure reactor as described above, for either 1 h or 4 h under 850 psi nitrogen with different catalysts. The results are shown in Table 4, which also includes results for Examples 28 and 31. These results demonstrate that the reaction time can be varied to improve HMF yield for a given set of conditions. Increasing the reaction time from 1 h to 4 h improved the LGone conversion and HMF yield for the sulfonic acid cation exchange resin catalyst at 120° C. and the phosphotungstic acid catalyst at 150° C.

TABLE 4

Results for Examples 28, 31, 34, and 35

| Ex | Catalyst | Loading (mg) | pH | Temp. (° C.) | Time (h) | Lgone Conversion (%) | HMF Yield (%) |
|---|---|---|---|---|---|---|---|
| 28 | DOWEX ™ (50WX8-400) sulfonic acid cation exchange resin | 15 | 3-4 | 120 | 1 | 72 | 21 |
| 34 | DOWEX ™ (50WX8-400) sulfonic acid cation exchange resin | 15 | 3-4 | 120 | 4 | 98 | 47 |
| 35 | Phosphotungstic acid hydrate | 2 | 3.0 | 150 | 1 | 69 | 14 |
| 31 | Phosphotungstic acid hydrate | 2 | 3.0 | 150 | 4 | 100 | 47 |

Examples 36-38

Conversion of Levoglucosenone to HMF with Different Catalyst Loadings

The reaction was performed in an 8-well pressure reactor as described above under 850 psi nitrogen with different catalysts. The results are shown in Table 5, which also includes results for Example 28, and demonstrate that the catalyst loading can be varied to improve HMF yield for a given set of conditions. For example, at 120° C., the HMF yield was increased for the sulfonic acid cation exchange resin by increasing the catalyst loading from 15 mg to 30 mg for a 1-hour run time, and for the H-Y catalyst by increasing the loading from 20 mg to 50 mg for a 4-hour run time.

TABLE 5

Results for Examples 36-38 and Example 28

| Ex | Catalyst | Loading (mg) | pH | Temp. (° C.) | Time (h) | Lgone Conversion (%) | HMF Yield (%) |
|---|---|---|---|---|---|---|---|
| 28 | DOWEX ™ (50WX8-400)sulfonic acid cation exchange resin | 15 | 3-4 | 120 | 1 | 72 | 21 |

TABLE 5-continued

Results for Examples 36-38 and Example 28

| Ex | Catalyst | Loading (mg) | pH | Temp. (° C.) | Time (h) | Lgone Conversion (%) | HMF Yield (%) |
|---|---|---|---|---|---|---|---|
| 36 | DOWEX ™ (50WX8-400)sulfonic acid cation exchange resin | 30 | 3-4 | 120 | 1 | 87 | 52 |
| 37 | H-Y (Si/Al = 40) CBV-780 | 20 | 4-5 | 120 | 4 | 69 | 10 |
| 38 | H-Y (Si/Al = 40) CBV-780 | 50 | 3-4 | 120 | 4 | 83 | 33 |

Examples 39 and 40

Conversion of 5-Hydroxymethyl-2-Furfural to a Product Mixture Comprising 2,5-furandimethanol and tetrahydro-2,5-furandimethanol Examples 39 and 40 were performed in an Endeavor Parallel Pressure Reactor (Biotage LLC, Charlotte, N.C.). The glass reaction vessel (RV) inserts were prepared for each Example as specified with a total weight of 5 g. HMF (0.25 g) was added to approximately 4.5 g of 10% water in tetrahydrofuran, followed by approximately 0.2 g catalyst slurry (50 wt % in water), as indicated in the Table below. The reaction vessels were loaded into the reactor block and the stirring was set at 450 RPM. The RVs were purged with nitrogen three times, then purged with $H_2$ three times, and then pressurized to 100 psi (0.69 MPa) with $H_2$ and heated to 100° C. over a period of 15 min. The pressure was then increased to 400 psi (2.76 MPa) and the RVs were left in this state for 3 h before heating was shut off and the RVs were left to cool below 50° C. The RVs were then removed from the reactor block and the reaction solutions were transferred to glass vials where they were diluted with water for a total mass of 14-20 g. All reaction solutions were then analyzed for the presence of HMF, FDM, and THFDM using HPLC. The results are shown in Table 6.

TABLE 6

Results for Examples 39 and 40

| Ex | Catalyst | Supplier | HMF Conversion | Yield FDM (%) | Yield THFDM (%) |
|---|---|---|---|---|---|
| 39 | Sponge Nickel, Fe promoted | Johnson Matthey | 100 | 25 | 63 |
| 40 | Activated Nickel, Fe and Cr promoted | Evonik Degussa | 98 | 0 | 90 |

Example 41

Conversion of tetrahydro-2,5-furandimethanol to a Product Mixture Comprising 1,6-hexanediol and 1,2,6-hexanetriol Using a $Pt/W/TiO_2$ Catalyst To a stainless steel (SS316) pressure reactor equipped with a magnetic stir bar and 5 ml of water were added 250 mg of 2,5-tetrahydrofurandimethanol (~95% pure) and about 250 mg of 4% $Pt/W/TiO_2$ catalyst. The reactor was sealed, connected to a high pressure gas manifold, and purged with nitrogen gas (1000 psi) three times. About 800 psi of hydrogen was then added and the reactor was heated to 160° C. After 6 h, the reactor was allowed to cool to room temperature within 2 h and depressurized. The reaction product solution was diluted with n-propanol and filtered through a standard 5 micron disposable filter. A sample was taken and analyzed by GC and GC/MS; results are given in Table 7.

TABLE 7

|  | THPM | 1,2-HD | 1,5-HD | 15PD | 1,6-HD | THFDM | 1,2,6-HT | other alcohols and byproducts |
|---|---|---|---|---|---|---|---|---|
| m [mg] | 2 | 2 | 10 | 0 | 132 | 7 | 53 | 6 |
| n [mmol] | 0.01 | 0.02 | 0.09 | 0 | 1.11 | 0.05 | 0.40 | ~0.05 |
| Yield | 1% | 1% | 5% | 0% | 62% | — | 22% | ~3% |

Example 42

Conversion of THFDM to a Product Mixture Comprising 1,6-HD and 1,2,6-HT Using a $Pt/W/TiO_2$ Catalyst at 160° C. and a 24 Hour Reaction Time Example 42 was conducted the same way as Example 41, but the reaction time was 24 h instead of 6 h. Results are given in Table 8.

TABLE 8

|  | THPM | 1,2-HD | 1,5-HD | 15PD | 1,6-HD | THFDM | 1,2,6-HT | others |
|---|---|---|---|---|---|---|---|---|
| m [mg] | 0.8 | 14.0 | 17.0 | 3.2 | 177.0 | 0.0 | 0.0 | ~8.4 |
| n [mmol] | 0.0 | 0.1 | 0.1 | 0.0 | 1.5 | 0.0 | 0.0 | n.d. |
| Yield | 0% | 7% | 4% | 2% | 83% | — | 0% | 4% |

Comparative Example A

5-Hydroxymethyl-2-furfural Concentration Over Time in 0.5 M HCl at 100° C.

Into a round-bottom flask, 5-hydroxymethyl-2-furfural (0.539 g, 4.27 mmol) was introduced with water (47.93 mL) and HCl (12 M, 2.066 mL, 25 mmol). The initial pH of the reaction mixture was 1.2. The reaction mixture was heated with stirring at 100° C. for 24 h with sampling at intervals. The samples were analyzed by GC to determine the amount of 5-hydroxymethyl-2-furfural present in solution; results are presented in Table 9. The data shows that the 5-hydroxymethyl-2-furfural concentration decreased with time, and that no 5-hydroxymethyl-2-furfural remained in the last sample taken. These results demonstrate that 5-hydroxymethyl-2-furfural is not stable at these reaction conditions.

TABLE 9

| Time mins | HMF concentration mg/g |
|---|---|
| 0 | 10.67 |
| 120 | 6.26 |
| 270 | 3.94 |
| 400 | 1.62 |
| 1350 (22.5 h) | 0 |

Comparative Example B

Heating of Levoglucosenone in Aqueous Solution at pH 10 and 100° C.

Into a round-bottom flask were added levoglucosenone (0.208 g, 1.65 mmol), water (4.0 mL), and sodium hydroxide (2 mg). The initial pH of the aqueous reaction mixture was 10. The reaction mixture was heated with stirring at 100° C. for 22 h with sampling at intervals. The samples were analyzed by GC to determine if HMF was present. No HMF was observed, demonstrating that under these conditions levoglucosenone was not converted to HMF.

Comparative Example C

Conversion of Levoglucosenone to HMF Using Sulfonic Acid Cation Exchange Resin at 100° C.

Into a round-bottom flask, LGone (0.202 g, 1.6 mmol) was introduced with water (4.04 g) and the sulfonic acid-based cation exchange resin DOWEX™ (50WX8-400, 112 mg). The initial pH was 3.5. The reaction was heated to 100° C. for 24 h with sampling at intervals. The samples were analyzed on the GC to determine 5-hydroxymethyl-2-furfural yield; results are shown in Table 10. After 22.5 h, the HMF yield was 23%.

TABLE 10

| Time mins | Yield of HMF mol % |
|---|---|
| 0 | 0 |
| 30 | 3 |
| 60 | 5 |
| 150 | 8 |
| 180 | 12 |
| 210 | 16 |
| 240 | 13 |
| 270 | 19 |
| 300 | 20 |
| 330 | 20 |
| 360 | 19 |
| 390 | 20 |
| 1350 | 23 |

What is claimed is:

1. A process comprising:
   a) contacting an aqueous reaction mixture comprising levoglucosenone with a catalyst, wherein the initial pH of the reaction mixture is between about 3 and about 6, and
   b) heating the reaction mixture at a temperature between about 120° C. and about 200° C. at a pressure of ambient pressure to about 1000 psi for a time sufficient to form a product mixture comprising 5-hydroxymethyl-2-furfural.

2. The process of claim 1, wherein the concentration of levoglucosenone is between about 1 wt % and about 50 wt %.

3. The process of claim 1, wherein the temperature is between about 120° C. and about 150° C.

4. The process of claim 1, wherein the pH is between about 3 and about 4.

5. The process of claim 1, wherein the catalyst is an acid catalyst.

6. The process of claim 1, wherein the catalyst is selected from the group consisting of glycolic acid, levulinic acid, benzoic acid, tungstic acid, and phosphotungstic acid hydrate.

7. The process of claim 1, wherein the catalyst is selected from the group consisting of sulfonic acid cation exchange resins, zeolite Y, montmorillonite, H-mordenite, and tungsten oxide.

8. The process of claim 1, wherein the catalyst comprises sulfonic acid cation exchange resins, zeolite Y, or phosphotungstic acid, the pH is between about 3 and about 4, and the temperature is about 150° C.

9. The process of claim 1, further comprising:
   c) heating the product mixture comprising 5-hydroxymethyl-2-furfural in the presence of hydrogen and a first hydrogenation catalyst at a temperature between about ambient temperature and about 120° C. at a pressure of about ambient pressure to about 1000 psi to form a second product mixture comprising one or more of 2,5-furandimethanol and tetrahydrofuran-2,5-dimethanol;
   d) separating the second product mixture from the first hydrogenation catalyst; and
   e) reacting the second product mixture with hydrogen in the presence of a second hydrogenation catalyst at a temperature between about 120° C. and about 260° C. at a pressure of about 800 psi to about 2000 psi to form a third product mixture comprising one or more of 1,2,6-hexanetriol, 2-hydroxymethyltetrahydropyran, and 1,6-hexanediol.

10. The process of claim 9, wherein the first hydrogenation catalyst comprises one or more of supported nickel catalysts, catalysts derived from nickel-aluminum alloys, catalysts derived from cobalt-aluminum alloys, supported ruthenium catalysts, supported rhodium catalysts, supported platinum catalysts, and supported palladium catalysts.

11. The process of claim 9, wherein the second hydrogenation catalyst comprises one or more of copper catalysts, supported platinum/tungsten catalysts, supported platinum catalysts, and supported palladium catalysts.

12. The process of claim 1, further comprising:
c) heating the product mixture comprising 5-hydroxymethyl-2-furfural in the presence of hydrogen and a hydrogenation catalyst at a temperature between about ambient temperature and 120° C. at a pressure of about ambient pressure to about 1000 psi for a time period of 10 minutes to 10 hours, and then at a temperature between about 120° C. and about 260° C. at a pressure of 800 psi to about 2000 psi for a sufficient time to form a second product mixture comprising one or more of 1,2, 6-hexanetriol, 2-hydroxymethyltetrahydropyran, and 1,6-hexanediol.

13. The process of claim 12, wherein the hydrogenation catalyst comprises one or more of copper catalysts, supported platinum/tungsten catalysts, supported platinum catalysts, and supported palladium catalysts.

\* \* \* \* \*